(12) United States Patent
Kim

(10) Patent No.: US 9,364,033 B2
(45) Date of Patent: Jun. 14, 2016

(54) SHOCK-ABSORBING DEVICE FOR HUMAN BODY

(75) Inventor: Choong-Hyun Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 398 days.

(21) Appl. No.: 14/000,938

(22) PCT Filed: Feb. 22, 2012

(86) PCT No.: PCT/KR2012/001328
§ 371 (c)(1),
(2), (4) Date: Aug. 22, 2013

(87) PCT Pub. No.: WO2012/115444
PCT Pub. Date: Aug. 30, 2012

(65) Prior Publication Data
US 2013/0326800 A1 Dec. 12, 2013

(30) Foreign Application Priority Data
Feb. 23, 2011 (KR) .................. 10-2011-0016172

(51) Int. Cl.
*A61B 5/00* (2006.01)
*A41D 13/015* (2006.01)
(Continued)

(52) U.S. Cl.
CPC .......... *A41D 13/0155* (2013.01); *A41D 13/018* (2013.01); *A41D 13/05* (2013.01); *A61B 5/1117* (2013.01); *A61B 5/1121* (2013.01)

(58) Field of Classification Search
CPC ...... A61B 5/11; A61B 5/1116; A61B 5/1117; A61B 5/1121; A61B 5/1123
USPC ....................................................... 600/595
See application file for complete search history.

(56) References Cited

U.S. PATENT DOCUMENTS 5,836,015 A    11/1998   Kristensen et al.
5,885,229 A *   3/1999   Yamato ................ A61B 5/1038
                                                           600/587
(Continued)

FOREIGN PATENT DOCUMENTS

JP   2007-084948 A   4/2007
KR   100842427 B1   6/2008

OTHER PUBLICATIONS

Hongwei Hsiao, et al; "Accuracy and precision of two in-shoe pressure mearsurement systems", Ergonomics, vol. 45, No. 8, pp. 537-555, Online Publication Date: Nov. 9, 2010.
(Continued)

*Primary Examiner* — Max Hindenburg
(74) *Attorney, Agent, or Firm* — Ladas & Parry LLP

(57) ABSTRACT

A shock-absorbing device for a human body which can reduce an impact applied to the human body when a wearer falls is provided. The shock-absorbing device for the human body includes: i) an airbag configured to surround the human body; ii) a compressed gas cartridge connected to the airbag and configured to store a gas to be injected into the airbag; iii) a compressed gas cartridge opener connected to the compressed gas cartridge and configured to eject the gas from the compressed gas cartridge; iv) a foot sensor placed at a foot of the human body and configured to sense and store a mass center of the human body; v) an acceleration sensor configured to sense a motion of the human body; vi) a fall detection sensor connected to the foot sensor and the acceleration sensor and configured to determine whether or not the human body is falling based on detection signals received from the foot sensor and the acceleration sensor, respectively; and vii) a control unit configured to control opening of the compressed gas cartridge opener in response to a signal received from the fall detection sensor. When the mass center detected by the foot sensor deviates from a sensing area, the fall detection sensor sends a fall signal to the control unit. When motion acceleration of the human body exceeds predetermined acceleration, the fall detection sensor can send another fall signal to the control unit.

20 Claims, 4 Drawing Sheets

(51) Int. Cl.
*A41D 13/018* (2006.01)
*A41D 13/05* (2006.01)
*A61B 5/11* (2006.01)

(56) References Cited

U.S. PATENT DOCUMENTS

| | | | |
|---|---|---|---|
| 6,920,647 B2 | 7/2005 | Ulert et al. | |
| 7,017,195 B2 | 3/2006 | Buckman et al. | |
| 7,150,048 B2 | 12/2006 | Buckman | |
| 7,690,051 B2 * | 4/2010 | Uchida | A62B 35/04 2/69 |
| 7,901,325 B2 * | 3/2011 | Henderson | A63B 24/0006 482/8 |
| 8,172,722 B2 * | 5/2012 | Molyneux | A43B 1/0054 434/247 |
| 8,246,354 B2 * | 8/2012 | Chu | A63B 22/0292 434/258 |
| 8,626,472 B2 * | 1/2014 | Solinsky | A61B 5/112 235/105 |
| 9,078,478 B2 * | 7/2015 | Ross, Jr. | A41D 27/10 |
| 9,176,932 B2 * | 11/2015 | Baggen | G06F 17/18 |
| 9,179,862 B2 * | 11/2015 | Stergiou | A61B 5/1038 |
| 9,179,864 B2 * | 11/2015 | Otto | A61B 5/1117 |
| 2006/0288464 A1 | 12/2006 | Warden | |

OTHER PUBLICATIONS

S.J. Dixon; "Use of pressure insoles to compare in-shoe loading for modern running shoes", Ergonomics, vol. 51, No. 10, pp. 1503-1514, Oct. 2008.
International Search Report; mailed Sep. 21, 2012; PCT/KR2012/001328.

* cited by examiner

SHOCK-ABSORBING DEVICE FOR HUMAN BODY

BACKGROUND OF THE INVENTION (a) Field of the Invention

The present invention relates to a shock-absorbing device for a human body. More particularly, the present invention relates to a shock-absorbing device for a human body which can reduce an impact on the human body when a person falls.

(b) Description of the Related Art

An aged person, a handicapped person who experiences serious aftereffects of a disease or injury, and a person who has a danger of an injury from a fall due to various recreation and sports or dangerous work environments may be subject to a bone fracture or a serious bruise due to an excessive load applied to a portion of the human body. For example, when a person falls, the hipbone or hip joint of the person can be injured due to a very great impact on the human body. Particularly, if a hip joint in which nerves and blood vessels are densely distributed is injured, it is very difficult to heal the injury. Accordingly, there is a need to develop a device capable of absorbing an impact applied to the human body in case of emergency because the above-described persons can be subject to serious stress disorders or can die when an excessive load is applied to the human body.

As conventional shock-absorbing techniques, a passive method of applying a shock-absorbing pad to a portion where an impact can be expected to occur, and an active method of wearing a fall detection sensor, detecting a fall using the sensor, and actuating an airbag, have been developed. Products using the existing techniques, however, are inconvenient to wear and are not particularly effective in shock-absorbing performance for the human body. Furthermore, the existing products are not efficacious because they do not properly detect falls even when the falls actually occur.

SUMMARY OF THE INVENTION

The present invention has been made in an effort to provide a shock-absorbing device for a human body, having advantages of precisely detecting a fall in real time and efficiently reducing an impact on the human body by actuating an airbag before a body part comes in contact with the ground.

An exemplary embodiment of the present invention provides a shock-absorbing device for the human body, including: i) an airbag configured to surround a hip, knee, head, neck, or wrist of the human body; ii) a compressed gas cartridge connected to the airbag and configured to store a gas to be injected into the airbag; iii) a compressed gas cartridge opener connected to the compressed gas cartridge and configured to eject the gas from the compressed gas cartridge; iv) a foot sensor placed at a foot of the human body and configured to sense and store a mass center of the human body; v) an acceleration sensor configured to sense a motion of the human body; vi) a fall detection sensor connected to the foot sensor and the acceleration sensor and configured to determine whether or not the human body is falling based on detection signals received from the foot sensor and the acceleration sensor, respectively; and vii) a control unit configured to control opening of the compressed gas cartridge opener in response to a signal received from the fall detection sensor. When the mass center detected by the foot sensor deviates from a sensing area, the fall detection sensor sends a fall signal to the control unit. When motion acceleration of the human body exceeds predetermined acceleration, the fall detection sensor may send another fall signal to the control unit.

Another embodiment of the present invention provides a shock-absorbing device for the human body, including: i) an airbag configured to surround a hip, knee, head, neck, or wrist of the human body; ii) a compressed gas cartridge connected to the airbag and configured to store a gas to be injected into the airbag; iii) a compressed gas cartridge opener connected to the compressed gas cartridge and configured to eject the gas from the compressed gas cartridge; iv) a foot sensor placed at a foot of the human body and configured to sense and store a mass center of the human body; v) an acceleration sensor configured to sense a motion of the human body; vi) a fall detection sensor connected to the foot sensor and the acceleration sensor and configured to determine whether or not the human body is falling based on detection signals received from the foot sensor and the acceleration sensor, respectively; and vii) a control unit configured to control opening of the compressed gas cartridge opener in response to a signal received from the fall detection sensor. When the mass center deviates from a sensing area and motion acceleration of the human body exceeds predetermined acceleration, the control unit determines whether or not a fall direction is a front direction of the human body.

The control unit may actuate the compressed gas cartridge opener if the fall direction is not the front direction of the human body. The fall detection sensor may send a fall signal to the control unit.

The shock-absorbing device for the human body in accordance with an exemplary embodiment of the present invention may further include clothes configured to cover the human body and have the airbag attached to the clothes. An electric wire for electrically coupling the foot sensor and the fall detection sensor may be fixed to the clothes. The clothes include a trouser unit covering a leg of the human body, and sewing holes into which the electric wire are inserted may be formed in the length direction of the trouser unit. The airbag may be detachably attached to the clothes and placed at a portion corresponding to a hip of the human body, and the airbag may be made of moisture-permeable and water proofing fabrics.

The shock-absorbing device for the human body in accordance with an exemplary embodiment of the present invention may further include a display unit connected to the control unit and configured to digitize and display a health state of the human body by converting information about motion of the human body. The shock-absorbing device for the human body in accordance with an exemplary embodiment of the present invention may further include a load sensor attached to the airbag and configured to sense weight of the human body, wherein the load sensor is connected to the display unit and configured to transmit a load sensed by the load sensor to the display unit. The shock-absorbing device for the human body in accordance with an exemplary embodiment of the present invention may further include a transmission unit configured to wirelessly send an operating state of the airbag if the airbag is connected to the control unit and actuated. Parts of the clothes corresponding to the genitals and anus of the human body may be opened.

The shock-absorbing device for the human body in accordance with an exemplary embodiment of the present invention has excellent wearing comfort and can more precisely determine whether a fall has occurred or not. Accordingly, an impact on the human body that may occur due to a fall can be minimized by effectively reducing an external impact transferred to the human body. As a result, direct and indirect medical expenses, such as medical expenses and nursing fees attributable to falls, task accident costs for the treatment of patients who are injured by falls, and social costs and economic costs attributable to premature death nationally can be significantly reduced. Furthermore, the shock-absorbing device for the human body can be extended and applied to elderly services/medical industries, to persons who are engaged in high-risk sports/leisure and at industrial sites, to persons who are engaged in various types of extreme sports, such as auto-bikes, mountain bikes, in-line skates, skate boards, water-skiing, sports climbing, and sky surfing, to persons who are exposed to high-risk industrial environments, such as the fabrication and repair of high-altitude steel towers and the cleaning of building walls, to the aged, or to patients.

DETAILED DESCRIPTION OF THE EMBODIMENTS

Technical terms used in this specification are intended to describe only specific exemplary embodiments and are not intended to restrict the present invention. The singular forms used in this specification include the plural forms unless specially described otherwise in sentences. Furthermore, a term such as "comprise" or "include" used in the specification materializes a specific characteristic, area, integer, step, operation, element, and/or component, and does not exclude the existence or addition of another specific characteristic, area, integer, step, operation, element, component, and/or group.

Unless defined otherwise, all terms including technical terms and scientific terms used in this specification have the same meanings as those commonly understood by a person having ordinary skill in the art to which the present invention pertains. Terms defined in a common dictionary are added and construed as having meanings that comply with related technical documents and disclosed contents, and are not construed as being ideal or very official meanings unless defined otherwise.

A meaning of "connection" used herein is construed as including all connection states, such as mechanical connection, as well as electrical connection. Accordingly, if objects are placed to influence one another even though a physical connection relationship between the objects is not established, the objects are constructed as being coupled together.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

Figure 1:
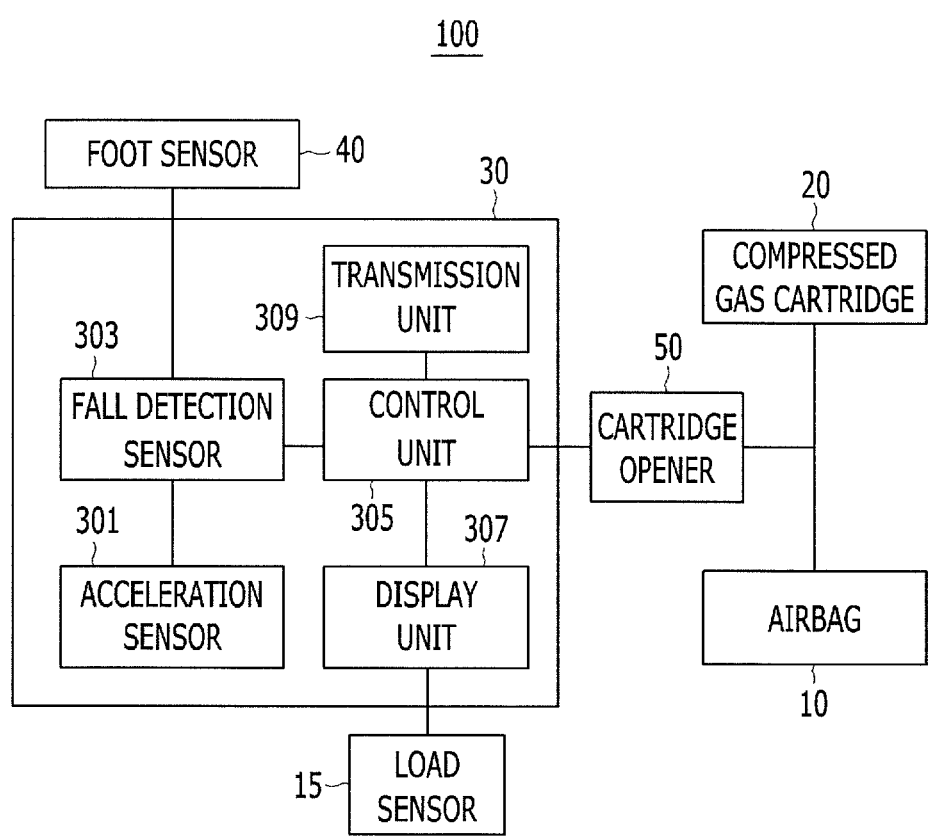
FIG. 1 is a schematic block diagram of a shock-absorbing device for the human body in accordance with an exemplary embodiment of the present invention.

FIG. 1 is a schematic block diagram of a shock-absorbing device for the human body in accordance with an exemplary embodiment of the present invention. The structure of the shock-absorbing device 100 for the human body shown in FIG. 1 has been provided to illustrate the present invention, but the present invention is not limited to the structure. Accordingly, the structure of the shock-absorbing device 100 for the human body can be modified differently.

As shown in FIG. 1, the shock-absorbing device 100 for the human body includes an airbag 10, a compressed gas cartridge 20, a main body 30, a foot sensor 40, a compressed gas cartridge opener 50, and a load sensor 15. The load sensor 15 may be omitted according to circumstances. Further, the main body 30 includes an acceleration sensor 301, a fall detection sensor 303, a control unit 305, a display unit 307, and a transmission unit 309. The display unit 307 and the transmission unit 309 may be omitted according to circumstances. Furthermore, although not shown in FIG. 1 for convenience, a power source is provided in the shock-absorbing device 100 for the human body in order to supply power to the elements.

The airbag 10 is inflated when compressed gas is rapidly injected into the airbag 10, thus surrounding and protecting the human body. That is, when a person who wears the airbag 10 falls, the airbag 10 is rapidly inflated, thus protecting the human body from a fall impact. The airbag 10 can be made of moisture-permeable and waterproofing fabrics in order to smoothly discharge sweat and prevent inflow of moisture from the outside. If the materials are used, the wearing comfort of the airbag 10 can be improved. Although not shown in FIG. 1, a film can be formed between the moisture-permeable and waterproofing fabrics, the edges of the moisture-permeable and waterproofing fabrics can be sealed and sewn, and an opening (not shown) can be formed in one edge of the film. That is, the airbag 10 is rapidly charged with gas injected into the airbag 10, but a specific amount of gas is externally discharged through the opening (not shown). In this case, a secondary impact due to the airbag 10 can be prevented from being applied to a person who wears the airbag 10. Meanwhile, the airbag 10 can be fabricated so that portions corresponding to the genitals and anus of the human body may be opened in order for an incontinent patient to be able to wear a diaper or various types of medical assistance appliances.

The compressed gas cartridge 20 is connected to the airbag 10 and configured to contain a gas to be injected into the airbag. When a fall of a wearer is detected and thus the compressed gas cartridge opener 50 is actuated, the compressed gas cartridge 20 is opened, so compressed gas within the compressed gas cartridge 20 is rapidly discharged externally. The rapidly discharged compressed gas flows into the airbag 10 and thus rapidly inflates the airbag 10. Further, the airbag 10 may be actuated when the compressed gas cartridge 20 is forcedly opened by pulling an external wire connected to the compressed gas cartridge 20.

As shown in FIG. 1, the compressed gas cartridge opener 50 is connected to the compressed gas cartridge 20. The compressed gas cartridge opener 50 ejects the gas stored in the compressed gas cartridge 20 from the compressed gas cartridge 20. The compressed gas cartridge opener 50 is actuated in response to a signal received from the control unit 305. Detailed constructions of the airbag 10, the compressed gas cartridge 20, and the compressed gas cartridge opener 50 can be readily understood by a person having ordinary skill in the art to which the present invention pertains, and thus a detailed description thereof is omitted.

Meanwhile, the acceleration sensor 301 of the main body 30 senses a motion of the human body. When a wearer falls, acceleration of motion of the wearer is increased greatly because fall speed is very great. Accordingly, whether or not the wearer is falling can be determined based on acceleration detected by the acceleration sensor 301. The acceleration sensor 301 senses acceleration of motion of the human body and sends the detected acceleration to the fall detection sensor 303. A detailed structure of the acceleration sensor 301 can be readily understood by a person having ordinary skill in the art to which the present invention pertains, and thus a detailed description thereof is omitted.

The foot sensor 40 provided separately from the acceleration sensor 301 is placed at a foot of the human body. Accordingly, the foot sensor 40 senses and stores the mass center of the human body. The foot sensor 40 is described in more detail below with reference to FIG. 2.

Figure 2:
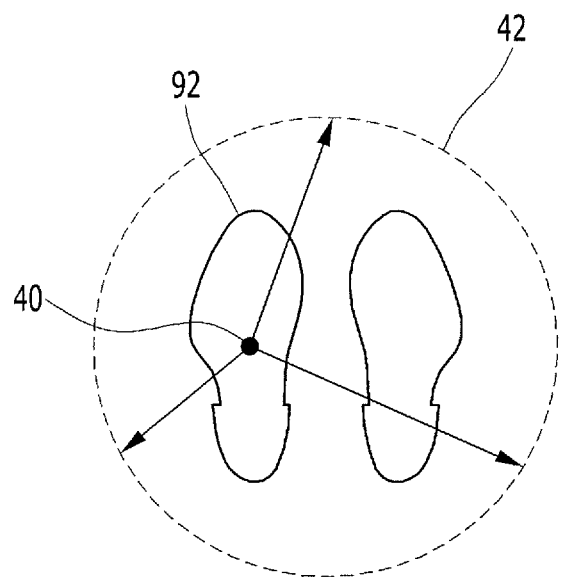
FIG. 2 is a diagram schematically showing a concept in which a foot sensor of FIG. 1 operates.

FIG. 2 is a diagram schematically showing a concept in which the foot sensor 40 of FIG. 1 operates. In FIG. 2, a sensing area 42 of the foot sensor 40 is indicated by a circle formed as a dotted line. The concept in which the foot sensor 40 operates in FIG. 2 illustrates the present invention, and the present invention is not limited thereto. Accordingly, the operating concept of the foot sensor 40 can be modified in other forms.

As shown in FIG. 2, the foot sensor 40 is attached to the bottom of a heal insert 902 (refer to FIG. 3) of shoes so that it is placed under a foot 92. The foot sensor 40 can be fabricated by inserting semiconductor ink of which electrical resistance is changed in inverse proportion to pressure applied to the foot sensor 40 into the circuits of the foot sensor. The foot sensor 40 analyzes the mass center by measuring the static and dynamic pressure distributions of the sole of the foot. The fall detection sensor 303 (refer to FIG. 1) can determine whether or not the mass center of the human body has deviated from the sensing area 42 by means of calculation using the signal of the foot sensor 40. If the measured center of mass has deviated from the sensing area 42, it can be seen that the human body is falling, and thus the airbag 10 (refer to FIG. 1) is actuated. The foot sensor 40 is used in robots, etc. Detailed contents of the foot sensor 40 can be readily understood by a person having ordinary skill in the art to which the present invention pertains, and thus a detailed description thereof is omitted.

Referring back FIG. 1, the fall detection sensor 303 is connected to the acceleration sensor 301 and the foot sensor 40. The fall detection sensor 303 determines whether or not the human body is falling using detection signals received from the acceleration sensor 301 and the foot sensor 40. That is, if motion acceleration of the human body detected by the acceleration sensor 301 exceeds a predetermined value and the mass center detected by the foot sensor 40 deviates from the sensing area 42, it can be determined that the human body is falling. In accordance with an exemplary embodiment of the present invention, accuracy in the operation of the shock-absorbing device 100 for the human body can be significantly improved because whether or not the human body is falling is determined using the acceleration sensor 301 and the foot sensor 40 at the same time, as described above. As a result, malfunction of the shock-absorbing device 100 for the human body can be prevented.

The control unit 305 controls the opening of the compressed gas cartridge opener 50 in response to a signal received from the fall detection sensor 303. That is, when the fall detection sensor 303 sends a signal informing that the human body is falling based on signals received from the acceleration sensor 301 and the foot sensor 40 to the control unit 305, the control unit 305 can generate and send a signal to actuate the compressed gas cartridge opener 50 based on such determination. In response thereto, the compressed gas cartridge opener 50 is opened and the compressed gas within the compressed gas cartridge 20 is injected into the airbag 10.

Accordingly, the airbag 10 can protect the human body from an impact attributable to the fall.

Meanwhile, the main body 30 can further include the display unit 307 and the transmission unit 309. The display unit 307 is connected to the control unit 305. The control unit 305 can digitize a health state of the human body by converting information about a motion of the human body, and the display unit 307 can digitize and display the health state. For example, the main body 30 can be used like a pace counter because the number of strides can be calculated and displayed using the display unit 307. Meanwhile, the control unit 305 or the display unit 307 may store information about a motion of the human body. Accordingly, a wearer can check his health state because the amount of motion or number of burned calories are calculated and displayed.

The transmission unit 309 of FIG. 1 can wirelessly send an operating state of the airbag 10 to the outside when the airbag 10 is actuated. That is, when the airbag 10 operates, it means that a wearer has fallen. In this case, the transmission unit 309 automatically informs an administrator who works in a sanatorium or a health management center of this state so that subsequent measures can be rapidly taken. For example, when an aged person falls, the location of the aged person is checked and direct relatives are immediately informed of this state by way of the transmission unit 309 so that the health of the aged person does not deteriorate further.

The load sensor 15 of FIG. 1 senses the weight of a wearer. The load sensor 15 is connected to the display unit 307 and configured to send a load value detected by the load sensor 15 to the display unit 307. Accordingly, if the load sensor 15 is attached to the airbag 10, the load of the human body can be checked through the display unit 307 because the weight of the human body when seated is transferred to the load sensor 15. Meanwhile, the load sensor 15 may monitor a change in the weight of a wearer and a sitting posture by periodically storing and providing a signal corresponding to a load. A state in which the shock-absorbing device 100 for the human body of FIG. 1 is actually used is described in more detail below with reference to FIG. 3.

Figure 3:
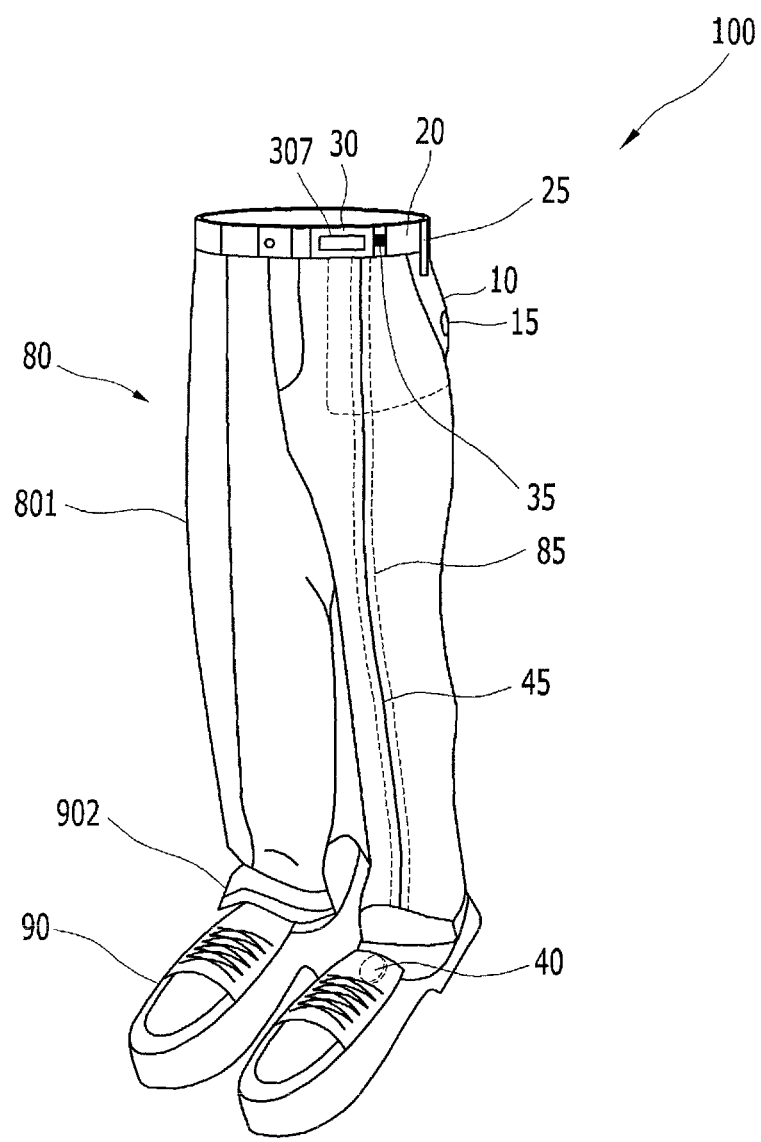
FIG. 3 is a schematic diagram showing the state in which the shock-absorbing device for the human body shown in FIG. 1 is used.

FIG. 3 is a schematic diagram showing the state in which the shock-absorbing device 100 for the human body shown in FIG. 1 is used. FIG. 3 illustrates the state in which the shock-absorbing device 100 for the human body is used in the present invention, and the present invention is not limited thereto. Accordingly, the state in which the shock-absorbing device 100 for the human body is used can be modified in various ways.

As shown in FIG. 3, the shock-absorbing device 100 for the human body can be attached to clothes 80. The shock-absorbing device 100 for the human body can be fabricated as a trouser type, an undergarment type, or a belt type. The airbag 10 surrounds the human body. The airbag 10 can be fabricated integrally with the clothes 80 or can be detachably attached to the clothes 80. The airbag 10 is placed at a portion corresponding to a hip of the human body. Particularly, the airbag 10 can be placed to surround a hip or both hip joints under the waist. Although not shown in FIG. 3, the airbag 10 may be attached to other joint portions where injuries are expected, such as the knee, the head, the neck, or the wrist of the human body.

The clothes 80 to which the airbag 10 is attached include a trouser unit 801. The clothes 80 are fabricated in a form to cover the human body. Although the clothes 80 have been illustrated as including only the trouser unit 801 in FIG. 3, the clothes 80 may be fabricated to include other parts, such as shirts. The load sensor 15 is attached to the airbag 10. Meanwhile, the clothes 80 can be fabricated so that portions corresponding to the genitals and anus of the human body may be opened in order for an incontinent patient to be able to wear a diaper or various types of medical assistant appliances.

As shown in FIG. 3 by a dotted line, sewing holes 85 are formed in the length direction of the trouser unit 801. The sewing holes 85 can be formed inside and outside the trouser unit 801. An electric wire 45 is inserted into the sewing holes 85 so that the electric wire 45 is fixed to the clothes 80.

As shown in FIG. 3, the foot sensor 40 can be inserted under the heal insert of the shoes 90. The foot sensor 40 is electrically connected to the fall detection sensor 303 (refer to FIG. 1) of the main body 30 through the electric wire 45. Although the foot sensor 40 has been illustrated as being connected to the main body 30 in FIG. 3 through the electric wire 45, the foot sensor 40 and the main body 30 may be coupled wirelessly.

The main body 30 is electrically connected to the compressed gas cartridge opener (not shown), placed in parallel to the compressed gas cartridge 20, through a connection line 35. When the compressed gas cartridge opener (not shown) is opened, the compressed gas within the compressed gas cartridge 20 is rapidly supplied to the airbag 10 through a compressed gas supply pipe 25. As a result, the human body can be protected from an impact resulting from a fall.

Meanwhile, the display unit 307 can be placed outside the main body 30 in order to check information about various motions of the human body. Although not shown in FIG. 3, the load sensor 15 is electrically connected to the display unit 307 through an internal electric wire.

Figure 4:
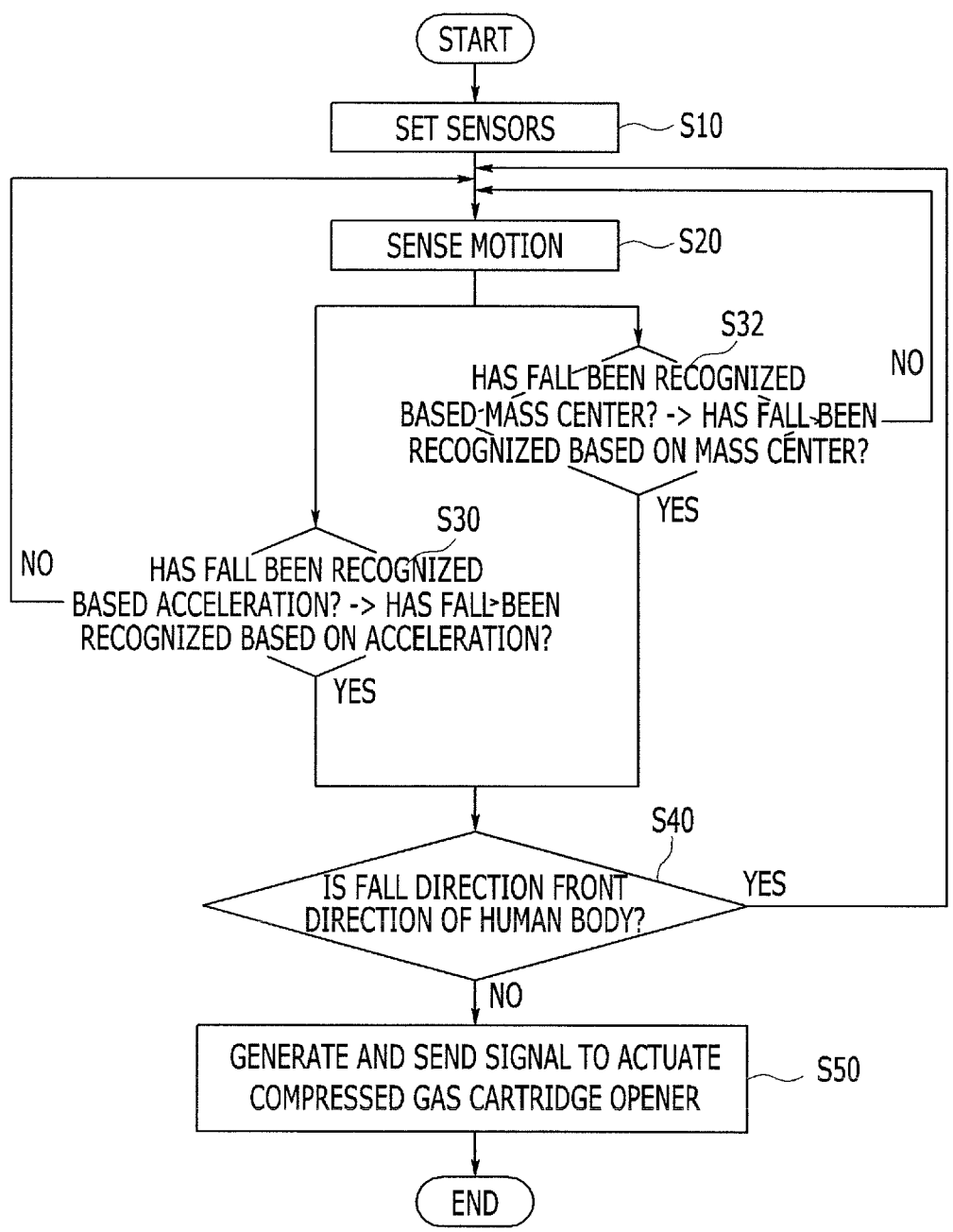
FIG. 4 is a schematic flowchart illustrating the operation of the shock-absorbing device for the human body shown in FIG. 1.

FIG. 4 is a schematic flowchart illustrating the operation of the shock-absorbing device 100 for the human body shown in FIG. 1. The order that the shock-absorbing device 100 for the human body operates in FIG. 4 illustrates the present invention, and the present invention is not limited thereto. Accordingly, the order that the shock-absorbing device 100 for the human body operates can be modified in various forms.

As shown in FIG. 4, first, the sensors are set at step S10. The sensors include the acceleration sensor, the foot sensor, and the fall detection sensor. Particularly, acceleration and a mass center each having a specific value are set in the fall detection sensor. Next, at step S20, a motion of the human body is detected by the sensors. That is, the acceleration sensor and the foot sensor sense acceleration and a mass center for a motion of the human body, respectively.

Next, at step S30, the fall detection sensor determines whether or not a fall has been recognized based on an acceleration signal received from the acceleration sensor. If measured acceleration exceeds a predetermined value, it is determined that the human body is falling. If it is determined that the human body is falling, the process proceeds to step S40. In contrast, if the measured acceleration is a predetermined value or lower, it is determined that the human body is in a normal state. Accordingly, the process returns back to step S20 in which the acceleration sensor continues to sense a motion of the human body.

Likewise, at step S32, the fall detection sensor determines whether or not a fall has been recognized based on a mass center signal received from the foot sensor. If the measured mass center is outside of the sensing area, it is determined that the human body is falling. When the fall is recognized, the process proceeds to step S40. In contrast, if the measured mass center is not outside of the sensing area, it means that the human body is in a normal state. Accordingly, the process returns back to step S20 in which the foot sensor continues to sense a motion of the human body.

Step S40 is performed only when a fall recognized based on measured acceleration at step S30 and when a fall is recognized based on the measured mass center at step S32. At step S40, the control unit finally determines whether or not a fall direction is the front direction of the human body based on the fall signal received from the fall detection sensor. If the fall direction is not the front direction of the human body, but is the rear direction or a lateral direction of the human body, a wearer can be in a dangerous situation. If the fall direction is not the front direction of the human body, the control unit immediately generates a signal to actuate the compressed gas cartridge opener and sends the generated signal to the compressed gas cartridge opener so that the airbag is actuated at step S50. As a result, the human body can be protected from an impact resulting from a fall. In contrast, if the fall direction is the front direction of the human body, the airbag does not need to be actuated because the fall can be prevented using a hand, etc. In this case, since the human body is in a normal state, the process returns back to step S20 in which the acceleration sensor and the foot sensor continue to sense a motion of the human body.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

DESCRIPTION OF REFERENCE NUMERALS

10. airbag
15. load sensor
20. compressed gas cartridge
25. compressed gas supply pipe
30. main body
40. foot sensor
42. sensing area
45. electric wire
50. cartridge opener
80. clothes
90. shoes
92. foot
100. shock-absorbing device for the human body
301. acceleration sensor
303. fall detection sensor
305. control unit
307. display unit
309. transmission unit
801. trouser unit
902. heal insert

What is claimed is:

1. A shock-absorbing device for a human body, comprising:
   an airbag configured to surround a hip, knee, head, neck, or wrist of the human body;
   a compressed gas cartridge connected to the airbag and configured to store a gas to be injected into the airbag;
   a compressed gas cartridge opener connected to the compressed gas cartridge and configured to eject the gas from the compressed gas cartridge;
   a foot sensor configured to be placed at a foot of the human body wherein the foot sensor comprises a circuit fabricated with a semiconductor ink that exhibits an electrical resistance inversely proportion to applied pressure in which the circuit is configured to measure static and dynamic pressure distributions from changes in the electrical resistance of the semiconductor ink to analyze and to store data corresponding to a center of mass of the human body;

an acceleration sensor configured to sense a motion of the human body;

a fall detection sensor connected to the foot sensor and the acceleration sensor and configured to determine whether or not the human body is falling based on detection signals received from the foot sensor and the acceleration sensor, respectively; and a control unit configured to control opening of the compressed gas cartridge opener in response to a signal received from the fall detection sensor, wherein when the center of mass detected by the foot sensor deviates from a sensing area, the fall detection sensor sends a fall signal to the control unit.

2. The shock-absorbing device of claim 1, wherein the fall detection sensor sends another fall signal to the control unit when motion acceleration of the human body exceeds a predetermined acceleration.

3. A shock-absorbing device for a human body, comprising:

an airbag configured to surround a hip, knee, head, neck, or wrist of the human body;

a compressed gas cartridge connected to the airbag and configured to store gas to be injected into the airbag;

a compressed gas cartridge opener connected to the compressed gas cartridge and configured to eject the gas from the compressed gas cartridge;

a foot sensor configured to be placed at a foot of the human body wherein the foot sensor comprises a circuit fabricated with a semiconductor ink that exhibits an electrical resistance inversely proportion to applied pressure in which the circuit is configured to measure static and dynamic pressure distributions from changes in the electrical resistance of the semiconductor ink to analyze and to store data corresponding to a center of mass of the human body;

an acceleration sensor configured to sense a motion of the human body;

a fall detection sensor connected to the foot sensor and the acceleration sensor and configured to determine whether or not the human body is falling based on detection signals received from the foot sensor and the acceleration sensor, respectively; and a control unit configured to control opening of the compressed gas cartridge opener in response to a signal received from the fall detection sensor, wherein when the center of mass deviates from a sensing area and motion acceleration of the human body exceeds predetermined acceleration, the control unit determines whether or not a fall direction is a front direction of the human body.

4. The shock-absorbing device of claim 3, wherein the control unit actuates the compressed gas cartridge opener if, as a result of the determination, it is determined that the fall direction is not the front direction of the human body.

5. The shock-absorbing device of claim 4, wherein the fall detection sensor sends a fall signal to the control unit.

6. The shock-absorbing device of claim 1, further comprising clothes configured to cover the human body and having the airbag attached to the clothes, wherein an electric wire for electrically coupling the foot sensor and the fall detection sensor is fixed to the clothes.

7. The shock-absorbing device of claim 6, wherein the clothes comprise a trouser unit covering a leg of the human body, and sewing holes into which the electric wire are inserted are formed in a length direction of the trouser unit.

8. The shock-absorbing device of claim 7, wherein the airbag is detachably attached to the clothes and placed at a portion corresponding to a hip of the human body, and the airbag is made of moisture-permeable and water proofing fabrics.

9. The shock-absorbing device of claim 1, further comprising a display unit connected to the control unit and configured to digitize and display a health state of the human body by converting information about motion of the human body.

10. The shock-absorbing device of claim 9, further comprising a load sensor attached to the airbag and configured to sense weight of the human body, wherein the load sensor is connected to the display unit and configured to transmit a load sensed by the load sensor to the display unit.

11. The shock-absorbing device of claim 1, further comprising a transmission unit configured to wirelessly send an operating state of the airbag if the airbag is connected to the control unit and actuated.

12. The shock-absorbing device of claim 6, wherein parts of the clothes corresponding to genitals and anus of the human body are opened.

13. A shock-absorbing device for wearing on a human body, the device comprising:

an airbag configured to surround a portion of the human body;

a gas cartridge connected to the airbag;

a foot sensor comprising a circuit fabricated with a semiconductor ink that exhibits an electrical resistance inversely proportion to applied pressure in which the circuit is configured to measure static and dynamic pressure distributions from changes in the electrical resistance of the semiconductor ink to analyze and to store data corresponding to a center of mass of the human body;

an acceleration sensor configured to sense a motion of the human body;

a fall detection sensor connected to the foot sensor and to the acceleration sensor wherein the fall detection sensor is configured to determine whether the human body is falling based on signals from the foot sensor and the acceleration sensor; and a control unit connected to the fall detection sensor and coupled to the gas cartridge, wherein the control unit is configured to control release of gas from the gas cartridge into the airbag in response to a signal from the fall detection sensor.

14. The shock-absorbing device of claim 13, wherein when the data corresponding to the center of mass center deviates from a sensing area then the fall detection sensor is configured to send a fall signal to the control unit that subsequently controls the release of gas from the gas cartridge into the airbag.

15. The shock-absorbing device of claim 13, further comprising a compressed gas cartridge opener connected between the gas cartridge and the control unit.

16. The shock-absorbing device of claim 13, wherein the portion of the human body is selected from the group consisting of a hip, a knee, a head, a neck and a wrist.

17. The shock-absorbing device of claim 13, further comprises clothing configured to cover the portion of the human body, wherein the airbag is attached to the clothing in which electric wires coupling the foot sensor and the fall detection sensor are fixed to the clothing.

18. The shock-absorbing device of claim 17, wherein the clothing comprises a trouser unit covering a leg of the human body, and sewing holes into which the electric wires are formed and inserted in a length direction of the trouser unit.

19. The shock-absorbing device of claim 17, wherein the airbag is detachably attached to the clothing and placed at a portion corresponding to a hip of the human body, and the airbag is made of moisture-permeable and water proofing fabrics.

20. The shock-absorbing device of claim 13, further comprising a display unit connected to the control unit and configured to digitize and display a health state of the human body by converting information about motion of the human body.

* * * * *